United States Patent [19]

Takaya et al.

[11] Patent Number: 5,563,295
[45] Date of Patent: Oct. 8, 1996

[54] PROCESS FOR PRODUCING OPTICALLY ACTIVE CARBOXYLIC ACID

[75] Inventors: Hidemasa Takaya, Shiga; Xiaoyong Zhang, Kanagawa; Kazuhiko Matsumura, Kanagawa; Noboru Sayo, Kanagawa; Hidenori Kumobayashi, Kanagawa, all of Japan

[73] Assignee: Takasago International Corporation, Tokyo, Japan

[21] Appl. No.: 399,549

[22] Filed: Mar. 7, 1995

[30] Foreign Application Priority Data

Mar. 8, 1994 [JP] Japan .................................. 6-036704

[51] Int. Cl.⁶ .................................................. C07B 53/00
[52] U.S. Cl. ...................... 562/606; 562/405; 562/496; 562/605
[58] Field of Search .................................. 562/405, 496, 562/605, 606

[56] References Cited

U.S. PATENT DOCUMENTS

| | | | |
|---|---|---|---|
| 4,962,230 | 10/1990 | Takaya et al. | 562/433 |
| 5,118,825 | 6/1992 | Wu | 556/21 |
| 5,190,905 | 3/1993 | Kolich et al. | 502/162 |
| 5,198,576 | 3/1993 | Scannell | 562/493 |
| 5,206,399 | 4/1993 | Sayo et al. | 556/20 |

FOREIGN PATENT DOCUMENTS

| | | |
|---|---|---|
| 0275354 | 7/1988 | European Pat. Off. . |
| 0479542 | 4/1992 | European Pat. Off. . |
| 64-9952 | 1/1989 | Japan . |

OTHER PUBLICATIONS

Tetrahedron Letters, vol. 32, No. 49, pp. 7283–7286 (1991).
Journal of the Chemical Society, Perkin Trans., pp. 2309–2322 (1994).

Primary Examiner—Gary Geist
Assistant Examiner—Barbara S. Frazier
Attorney, Agent, or Firm—Sughrue, Mion, Zinn, Macpeak & Seas

[57] ABSTRACT

A process for the production of an optically active carboxylic acid (I), which comprises subjecting an olefinic carboxylic acid (II) to asymmetric hydrogenation using a complex as a catalyst consisting of an optically active phosphine (III) and a ruthenium compound.

Complex of

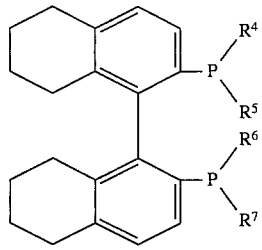

with a ruthenium compound

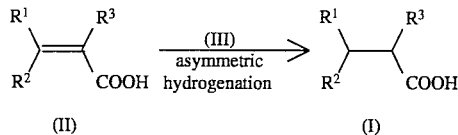

According to the process of the present invention, optically active carboxylic acids can be produced with high yield.

5 Claims, No Drawings

PROCESS FOR PRODUCING OPTICALLY ACTIVE CARBOXYLIC ACID

FIELD OF THE INVENTION

This invention relates to a process for the high yield production of optically active carboxylic acids which are useful in the field of medicines and agricultural chemicals.

BACKGROUND OF THE INVENTION

In the field of medicines and agricultural chemicals, one of the optical isomers of a compound shows especially excellent action in many cases. Particularly, a large number of optically active substances of carboxylic acids show excellent properties when each substance has an asymmetric carbon atom at the α- or β-position.

With regard to the synthesis of these optically active carboxylic acids by asymmetric hydrogenation reaction, there are known processes in which a complex of an optically active phosphine compound with a transition metal is used as a catalyst of the asymmetric hydrogenation. Examples of such processes include a process which uses a complex of a phosphine having an optically active binaphthyl structure with ruthenium (JP-A-63-239245; the term "JP-A" as used herein means an "unexamined published Japanese patent application") and a process for the production of optically active phenylacetic acid derivatives using a complex of a transition metal with a phosphine having an optically active binaphthyl structure (JP-A-64-9952).

However, the prior art processes described above are defective in that the asymmetric yield of the reaction product is generally low although the product has a high optical purity, or that the optical purity of the reaction product is low although the asymmetric yield thereof is high. Namely, the above processes have failed to attain both a satisfactory optical purity and a satisfactory asymmetric yield. The prior art processes therefore are not industrially advantageous processes.

SUMMARY OF THE INVENTION

In view of the above, it therefore becomes an object of the present invention to provide a process by which optically active carboxylic acids can be produced with a high yield.

As a result of intensive studies, the inventors of the present invention have found that optically active carboxylic acids can be produced with a high asymmetric yield which cannot be attained by the prior art process, by the use of a complex as an asymmetric hydrogenation catalyst which consists of a ruthenium compound and a phosphine having a 5,5',6,6',7,7',8,8'-octahydrobinaphthyl structure instead of a phosphine having an optically active binaphthyl structure. The present invention has been accomplished on the basis of this finding.

The process of the present invention for the production of an optically active carboxylic acid is summarized by the following reaction formula.

Complex of

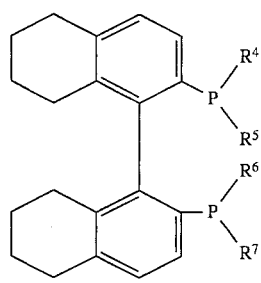

with a ruthenium compound

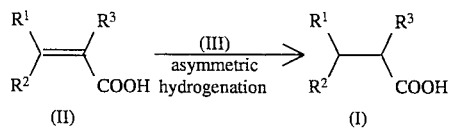

In the above reaction formula, $R^1$, $R^2$ and $R^3$ each represents a hydrogen atom, an alkyl group which may have a substituent group or an aromatic hydrocarbon group which may have a substituent group, with the proviso that $R^1$, $R^2$ and $R^3$ are not hydrogen atoms at the same time, that $R^3$ is a group other than methyl when $R^1$ and $R^2$ are hydrogen atoms at the same time, and that $R^1$ and $R^2$ are different groups other than a lo hydrogen atom when $R^3$ is a hydrogen atom; and $R^4$, $R^5$, $R^6$ and $R^7$ may be the same or different from one another and each represents a phenyl group which may be substituted with an alkyl group having 1 to 4 carbon atoms, an alkoxy group having 1 to 4 carbon atoms or a halogen atom, a cyclopentyl group or a cyclohexyl group.

Accordingly, the present invention provides a process for the production of an optically active carboxylic acid represented by the above formula (I), which comprises subjecting an olefinic carboxylic acid represented by the above formula (II) to asymmetric hydrogenation using, as a catalyst, a complex of an optically active phosphine represented by the above formula (III) with a ruthenium compound.

Other objects and advantages of the present invention will be made apparent as the description progresses.

DETAILED DESCRIPTION OF THE INVENTION

In formula (II) which represents the olefinic carboxylic acid to be used in the process of the present invention, examples of the alkyl group represented by $R^1$, $R^2$ and $R^3$, which may have a substituent group, include straight- or branched-chain alkyl groups each having 1 to 8 carbon atoms, which may be substituted, for example, with a halogen atom, a hydroxy group, an alkoxy group having 1 to 6 carbon atoms and an alkanoyloxy group having 2 to 6 carbon atoms. Illustrative examples of said alkyl group include methyl, ethyl, n-propyl, isopropyl, n-butyl, isobutyl, tert-butyl, n-pentyl, n-hexyl, n-heptyl, n-octyl and the like groups. Illustrative examples of the halogen atom to be used as a substituent on the alkyl group include chlorine, fluorine, bromine and iodine. Illustrative examples of the aforementioned alkoxy group include methoxy, ethoxy, n-propyloxy, isopropyloxy, n-butyloxy, n-pentyloxy and the like groups. Illustrative examples of the aforementioned alkanoyloxy group include acetoxy, propanoyloxy, butylyloxy and the like groups.

Illustrative examples of the aromatic hydrocarbon group include phenyl, naphthyl, biphenyl and the like groups which may have a substituent group such as an alkyl group having 1 to 6 carbon atoms, an alkoxy group having 1 to 6 carbon atoms, a halogen atom, an aroyl group and the like.

In this case, the alkyl group, halogen atom and alkoxy group may be selected from the aforementioned illustrative examples, and benzoyl may be used as the aroyl group.

Preferred examples of $R^1$ include a hydrogen atom, an alkyl group having 1 to 8 carbon atoms and a halogen-substituted alkyl group having 1 to 8 carbon atoms, and preferred examples of $R^2$ and $R^3$ include a hydrogen atom, an alkyl group having 1 to 8 carbon atoms, a halogen-substituted alkyl group having 1 to 8 carbon atoms, a hydroxy-substituted alkyl group having 1 to 8 carbon atoms, an alkyl group having 1 to 8 carbon atoms which is substituted with an alkanoyl group of 2 to 6 carbon atoms, a phenyl, biphenyl or naphthyl group which may be substituted with an alkyl group of 1 to 6 carbon atoms, an alkoxy of 1 to 6 carbon atoms or a halogen atom and a benzoylphenyl group.

Illustrative examples of the olefinic carboxylic acid (II) include 3-methylcinnamic acid, 3-methyl-4-hydroxy-2-butenoic acid, 3-methyl-4-acetoxy-2-butenoic acid, 3-methyl- 5-hydroxy-2-pentenoic acid, 3-methyl-5-acetoxy-2-pentenoic acid, 2-methyl-4-hydroxy-2-butenoic acid, 2-methyl-4-acetoxy- 2-butenoic acid, 2-(hydroxymethyl)-2-butenoic acid, 2 -(acetoxymethyl)-2-butenoic acid, 2-methyl-2-octenoic acid, 2 -methyl-2-heptenoic acid, 2-methyl-2-hexenoic acid, 2-methyl- 2-nonenoic acid, 2-methyl-2-decenoic acid, 3-methyl-2-pentenoic acid, 3-methyl-2-hexenoic acid, 3-methyl-2-heptenoic acid, 3-methyl-2-octenoic acid, 3-methyl-2-nonenoic acid, 3-methyl-2-decenoic acid, 2-ethyl-2-butenoic acid, 2 -ethyl-2-pentenoic acid, 2-ethyl-2-heptenoic acid, 2-ethyl-2-octenoic acid, 2-ethyl-2-nonenoic acid, 2-ethyl-2-decenoic acid, 3-trifluoromethyl-2-butenoic acid, 2-(4isobutylphenyl)propenoic acid, 2-(3-benzoylphenyl)propenoic acid, 2-(2-fluoro-1,1'-biphenyl-4-yl)propenoic acid, 2-(6-methoxynaphthyl)propenoic acid and the like.

Examples of the compound to be produced by the process of the present invention include optically active carboxylic acids in which the α- and β-positions of the above compounds are hydrogenated.

In the optically active phosphine (III) for use in the present invention, $R^4$, $R^5$, $R^6$, and $R^7$ may be the same or different and each represents a phenyl group which may be substituted with an alkyl group having 1 to 4 carbon atoms, an alkoxy group having 1 to 4 carbon atoms, or a halogen atom, a cyclopentyl group, or a cyclohexyl group.

Examples of the optionally substituted phenyl group include phenyl groups substituted with an alkyl group having 1 to 4 carbon atoms, e.g., o-tolyl, m-tolyl, p-tolyl, and 3,5-dimethylphenyl; phenyl groups substituted with an alkoxy group having 1 to 4 carbon atoms, e.g., o-methoxyphenyl, m-methoxyphenyl, p-methoxyphenyl, and 3,5-dimethoxyphenyl; and halogen-substituted phenyl groups, e.g., p-fluorophenyl, p-chlorophenyl, m-chlorophenyl, o-chlorophenyl, p-iodophenyl, p-bromophenyl, and 3,5-dichlorophenyl.

The phosphine (III) to be used in the present invention exists in two optically active forms (+) and (−), and both forms can be applied to the process of the present invention. In addition, the phosphine to be used in the present invention can be produced, for example, in accordance with the procedure disclosed in JP-A-4-139140, more particularly in accordance with the following reaction formula.

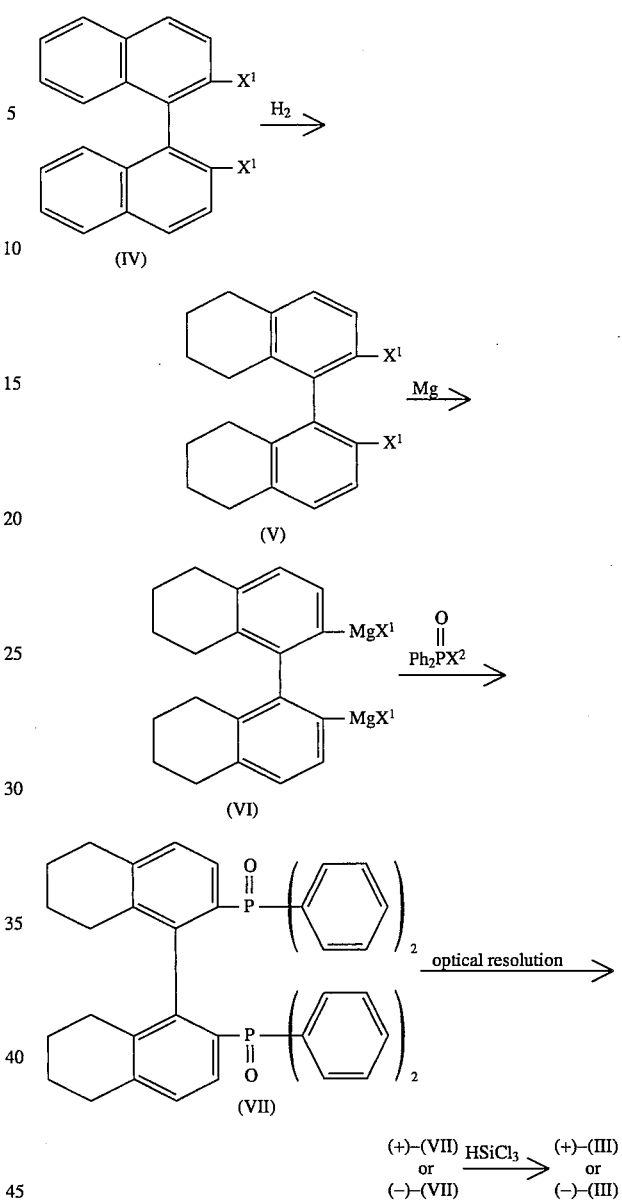

In the above formula, $X^1$ and $X^2$ each represents a halogen atom.

That is, 2,2'-dihalogeno-1,1'-binaphthyl (IV) is hydrogenated in the presence of a ruthenium-carbon catalyst to convert it into 2,2'-dihalogeno-5,5',6,6',7,7',8,8'-octahydro-1,1'-binaphthyl (V) which is subsequently allowed to react with metallic magnesium to form Grignard's reagent (VI) and then subjected to condensation with diphenylphosphinyl halide to obtain 2,2'-bis(diphenylphosphoryl)- 5,5',6,6',7,7', 8,8'-octahydro-1,1'-binaphthyl (VII).

The starting material 2,2'-dibromo-1,1'-binaphthyl (IV) can be synthesized for example in accordance with the method of Takaya et al. (*J. Org. Chem.*, vol. 51, p. 629, 1986), and its hydrogenation is carried out for 15 to 25 hours under a hydrogen pressure of from 50 to 150 kg/cm² and at a temperature of from 70° to 120° C. in the presence of a ruthenium-carbon catalyst.

Reaction of the compound (V) with metallic magnesium and reaction of the thus obtained Grignard's reagent (VI) with diphenylphosphinyl halide may be effected by the conventional Grignard reaction.

The racemic compound (VII) is recrystallized from a chloroform-ethyl acetate mixture solvent using optically active dibenzoyltartaric acid as a resolving agent, collected by filtration and then made into phosphine oxide by its treatment with 1N sodium hydroxide. By checking its optical purity by high performance liquid chromatography using an optically active column (CHIRALCEL OG, manufactured by Daicel Chemical Industries), recrystallization of the diastereomer is repeated until it becomes optically pure. A (−) form of the compound (VII) is precipitated as a diastereomer when (−)-dibenzoyltartaric acid is used in the optical resolution, and a (+) form of the compound (VII) is precipitated as a diastereomer when (+)-dibenzoyltartaric acid is used in the optical resolution.

The resulting (−)-(VII) or (+)-(VII) compound is reduced with trichlorosilane in the usual way to obtain the (+) or (−) form of the phosphine (III) to be used in the present invention.

Illustrative examples of the phosphine as a raw material of the complex to be used in the process of the present invention include 2,2'-bis(diphenylphosphino)-5,5',6,6',7,7',8,8'-octahydro-1,1'-binaphthyl (H$_8$-binap) (to be referred to as "OcH-binap" hereinafter), 2,2'-bis(dicyclohexylphosphino)-5,5',6,6',7,7',8,8'-octahydro-1,1'-binaphthyl (to be referred to as "Cy-binap" hereinafter), 2,2'-bis(dicyclopentylphosphino)-5,5',6,6',7,7',8,8'-octahydro- 1,1'-binaphthyl (to be referred to as "Cp-binap" hereinafter), 2,2'-bis(di(p-tolyl)phosphino)-5,5',6,6',7,7',8,8'-octahydro- 1,1'-binaphthyl (to be referred to as "pT-binap" hereinafter), 2,2'-bis(di(p-chlorophenyl)phosphino)-5,5',6,6',7,7',8,8'-octahydro-1,1'-binaphthyl (to be referred to as "Cl-binap" hereinafter), 2,2,-bis(di(p-methoxyphenyl)phosphino)-5,5', 6,6',7,7',8,8'-octahydro-1,1'-binaphthyl (to be referred to as "Mo-binap" hereinafter), 2,2'-bis(di(3,5-xylyl)phosphino)-5,5',6,6',7,7',8,8'-octahydro- 1,1'-binaphthyl (to be referred to as "Xy-binap" hereinafter) and 2,2'-bis(di(t-butylphenyl)phosphino)-5,5',6,6',7,7',8,8'-octahydro-1,1'-binaphthyl (to be referred to as "Bu-binap" hereinafter).

Examples of the ruthenium compound which forms a complex with the phosphine include compounds represented by the following formula (VIII) or (IX):

$$[RuX_2Q^1]_n \quad (VIII)$$

wherein X represents a halogen atom, an allyl group, or a methallyl group, Q$^1$ represents 1,5-cyclooctadiene, norbornadiene, benzene, or p-cymene, and n represents a natural number;

$$RuA_3 \quad (IX)$$

wherein A represents acetylacetonato or an acetoxy group.

Specific examples of the ruthenium compound include [RuCl$_2$(COD)]$_n$ (herein, COD represents 1,5-cyclooctadiene and n means a natural number), [RuBr$_2$(COD)]$_n$, [RuCl$_2$(NBD)]$_n$ (herein, NBD represents norbornadiene), [RuBr$_2$(NBD)]$_n$, [RuCl$_2$(benzene)]$_2$, [RuBr$_2$(benzene)]$_2$, [RuI$_2$(benzene)]$_2$, [RuCl$_2$(p-cymene)]$_2$, [RuBr$_2$(p-cymene)]$_2$, [RuI$_2$(p-cymene)]$_2$, [(allyl)$_2$Ru(COD)]$_2$, [(allyl)$_2$Ru(NBD)]$_2$, [(methallyl)$_2$Ru(COD)]$_2$, [(methallyl)$_2$Ru(NBD)]$_2$, Ru(acac)$_3$ (herein, acac represents acetylacetonato) and Ru(OAC)$_3$ (herein, Ac represents acetyl group).

Examples of the complex for use in the present invention, which is formed from the phosphine compound (III) and the ruthenium compound, include compounds represented by the following formula (X), (XI), or (XII):

$$Ru_2Y_4LA \quad (X)$$

wherein Y represents a halogen atom, L represents an optically active phosphine compound represented by the following formula (III):

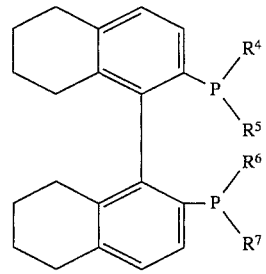

(wherein R$^4$, R$^5$, R$^6$, and R$^7$ are the same as defined above), and A represents a tertiary amine;

$$RuZ_2L \quad (XI)$$

wherein Z represents an acetoxy group, an acetylacetonato, an allyl group, or a methallyl group and L is the same as defined above;

$$[RuYQ^2L]X \quad (XII)$$

wherein Y and L are the same as defined above and Q$^2$ represents p-cymene or benzene.

Examples of the tertiary amine represented by A in the above compound (X) include tri(lower alkyl)amines and triphenylamine. Preferred tri(lower alkyl)amines are those in which each alkyl has 1 to 4 carbon atoms, e.g., trimethylamine, triethylamine, and tripropylamine.

Examples of the halogen atom represented by X and Y include a fluorine atom, bromine atom, iodine atom, and chlorine atom.

Specific examples of the complex include Ru$_2$Cl$_4$(OcH-binap)(NEt$_3$), Ru$_2$Cl$_4$(Cy-binap)(NEt$_3$), Ru$_2$Cl$_4$(Cp-binap)(NEt$_3$), Ru$_2$Cl$_4$(pT-binap)(NEt$_3$), Ru$_2$Cl$_4$(Cl-binap)(NEt$_3$), Ru$_2$Cl$_4$(Mo-binap)(NEt$_3$), Ru$_2$Cl$_4$(Xy-binap)(NEt$_3$), Ru$_2$Cl$_4$(Bu-binap)(NEt$_3$), Ru(OAc)$_2$(OcH-binap), Ru(OAc)$_2$(Cy-binap), Ru(OAc)$_2$(Cp-binap), Ru(OAc)$_2$(pT-binap), Ru(OAc)$_2$(Cl-binap), Ru(OAc)$_2$(Mo-binap), Ru(OAc)$_2$(Xy-binap), Ru(OAc)$_2$(Bu-binap), Ru(acac)$_2$(OcH-binap), Ru(acac)$_2$(Cy-binap), Ru(acac)$_2$(Cp-binap), Ru(acac)$_2$(pT-binap), Ru(acac)$_2$(Cl-binap), Ru(acac)$_2$(Mo-binap), Ru(acac)$_2$(Xy-binap), Ru(acac)$_2$(Bu-binap), [RuI(p-cymene)(OcH-binap)]I, [RuI(p-cymene)(Cy-binap)]I, [RuI(benzene)(Cp-binap)]I, [RuI(p-cymene)(pT-binap)]I, [RuI(benzene)(Cl-binap)]I, [RuI(p-cymene)(Mo-binap)]I, [RuI(benzene)(Xy-binap)]I, [RuI(p-cymene)(Bu-binap)]I, [RuCl(p-cymene)(OcH-binap)]Cl, [RuCl(benzene)(Cy-binap)]Cl, [RuCl(p-cymene)(Cp-binap)]Cl, [RuCl(p-cymene)(pT-binap)]Cl, [RuCl(benzene)(Cl-binap)]Cl, [RuCl(benzene)(Mo-binap)]Cl, [RuCl(p-cymene)(Xy-binap)]Cl, [RuCl(p-cymene)(Bu-binap)]Cl, [RuBr(benzene)(OcH-binap)]Br, [RuBr(p-cymene)(Cy-binap)]Br, [RuBr(p-cymene)(Cp-binap)]Br, [RuBr(benzene)(pT-binap)]Br, [RuBr(p-cymene)(Cl-binap)]Br, [RuBr(p-cymene)(Mo-binap)]Br, [RuBr(benzene)(Xy-binap)]Br, [RuBr(p-cymene)(Bu-binap)]Br, Ru(OcH-binap)(allyl)$_2$, Ru(Cy-binap)(methallyl)$_2$, Ru(Cp-binap)(methallyl)$_2$, Ru(pT-binap)(allyl)$_2$, Ru(Cl-binap)(allyl)$_2$, Ru(Mo-binap)(methallyl)$_2$, Ru(Xy-binap)(allyl)$_2$ and Ru(Bu-binap)(allyl)$_2$.

These complexes can be produced for example by the following methods.

(1) Ru$_2$Cl$_4$(L)$_2$(NEt$_3$)

(The term "L" as used herein means the optically active phosphine represented by formula (III).)

In the same manner as the method for the synthesis of Ru$_2$Cl$_4$(binap)(NEt$_3$) (the term "binap" as used herein means 2,2'-diphenylphosphino-1,1'-binaphthyl) disclosed by T. Ikariya et al. in *J. Chem. Soc. Chem. Commun.*, p. 992 (1985), Ru$_2$Cl$_4$(L)$_2$(NEt$_3$) can be obtained by subjecting [RuCl$_2$(COD)]$_n$ which is easily obtainable from ruthenium chloride and COD to heating reaction with the compound L of the present invention in toluene solvent in the presence of triethylamine.

(2) Ru(OAc)$_2$(L) type complex

This complex can be obtained as a crude product in accordance with the procedure disclosed in JP-A-62-265293 by allowing Ru$_2$Cl$_4$(L)$_2$(NEt$_3$) and a carboxylate to react with each other in an alcohol solvent such as methanol, ethanol, t-butanol or the like at a temperature of from about 20° to 110° C. for 3 to 15 hours, removing the solvent by distillation, extracting the complex of interest with a solvent such as ether, ethanol or the like and then evaporating the extract to dryness. This product may be used as a catalyst for asymmetric hydrogenation reaction and the like as it is or after its further purification by recrystallization using a solvent such as ethyl acetate or the like.

The material Ru$_2$Cl$_4$(L)$_2$(NEt$_3$) can be obtained in accordance with the process disclosed in JP-A-61-63690.

A complex having a trifluoroacetate group can be obtained by allowing the diacetate complex Ru(L)(O$_2$CCH$_3$) prepared above to react with trifluoroacetic acid at about 25° C. for about 12 hours using methylene chloride as the solvent.

(3) Ru(acac)$_2$(L) type complex

This complex can be synthesized in accordance with the process disclosed in JP-A-5-271263. That is, it can be produced by allowing a Ru(III) species such as Ru(acac)$_3$ to react with a reducing agent such as zinc powder in an appropriate solvent such as ethanol in the presence of an L ligand.

(4) [RuCl(p-cymene)(L)]Cl type complex

This complex can be obtained by preparing [RuCl$_2$(Ar)]$_2$ (Ar represents p-cymene or benzene) in accordance with the method described in *J. Org. Chem.*, vol. 7, p. 487 (1976) or *Can. J. Chem.*, vol. 50, p. 3643 (1972), allowing the thus prepared starting material to react with the compound L at 25° to 50° C. for 30 minutes to 3 hours in a single solvent such as methanol, ethanol, benzene, methylene chloride or the like or a mixed solvent thereof and then removing the solvent under a reduced pressure.

Alternatively, when [RuBr(Ar)(L)]Br or [RuI(Ar)(L)]I is produced, [RuZ$_2$(Ar)]$_2$ (Z represents bromine or iodine atom) is firstly prepared, for example, by allowing [RuCl$_2$(Ar)]$_2$ as the staring material to react with an alkali metal halide such as NaBr, NaI or the like using water as the solvent, or by allowing [RuCl$_2$(Ar)]$_2$ to react with an alkali metal halide at room temperature in a water-methylene chloride solvent using a quaternary ammonium salt or a quaternary phosphonium salt as a phase-transfer catalyst. The phase-transfer catalyst (VIII) may be selected, for example, from those which are disclosed in *Phase-Transfer Catalysts* (edited by W. P. Weber and G. W. Gokel, translated by I. Tabuse and T. Nishiya, the first edition by Kagaku Dojin, 1978-9-5). Next, the thus prepared [RuZ$_2$(Ar)]$_2$ is allowed to react with the compound L at 25° to 50° C. for 30 minutes to 3 hours in a single solvent such as methanol, ethanol, benzene, methylene chloride or the like or a mixed solvent thereof and then the solvent is removed under a reduced pressure, thereby effecting quantitative synthesis of [RuBr(Ar)(L)]Br or [RuI(Ar)(L)]I.

(5) Ru(L)(methallyl)$_2$ type complex

In accordance with the method described in *J. Chem. Soc., (A)* 159, 1968, 2-methyl-1-propenyl chloride is allowed to react with magnesium in ether to synthesize Grignard's reagent which is subsequently allowed to react with [Ru(COD)Cl$_2$]$_n$ to obtain [(methallyl)$_2$Ru(COD)]$_2$. Thereafter, Ru(L)(methallyl)$_2$ is synthesized by allowing the thus obtained [(methallyl)$_2$Ru(COD)]$_2$ to react with the phosphine L in a hydrocarbon solvent such as hexane or toluene.

In the process of the present invention for the production of optically active carboxylic acids, the ruthenium-phosphine complex may be used in an amount of from 1/50 to 1/1,000 mol, preferably from 1/100 to 1/500 mol, more preferably from 1/150 to 1/300 mol, per 1 mol of the raw material olefinic derivative.

The asymmetric hydrogenation reaction is generally carried out in a solvent. Examples of such solvent to be used herein include one or more solvents selected from alcohol solvents such as methanol, ethanol, isopropyl alcohol, butanol and the like, esters such as methyl acetate, ethyl acetate and the like, tetrahydrofuran and water, of which methanol, ethanol or tetrahydrofuran or a mixture of water therewith is particularly preferred.

This reaction may be carried out under a hydrogen pressure of preferably from 1 to 200 kg/cm$^2$, more preferably from 1 to 150 kg/cm$^2$, most preferably from 1 to 100 kg/cm$^2$. In some cases, the reaction may progress more smoothly when a tertiary amine such as triethylamine, tri-n-propylamine or the like is added to the reaction system in an amount of from 1 to 5 molar equivalents, preferably from 1 to 2 molar equivalents, to the substrate.

The catalyst for use in the present invention is further explained below. In the present invention, the optically active phosphine compound (III) and the ruthenium compound may be separately added to conduct the reaction. Alternatively, a ruthenium-optically active phosphine complex may be first obtained from the optically active phosphine compound (III) and the ruthenium compound before this complex is added to conduct the reaction.

The optically active carboxylic acids obtained in the aforementioned manner are useful as medicines, agricultural chemicals, raw materials thereof or intermediates thereof.

Thus, according to the present invention, optically active carboxylic acids can be produced with a high yield.

EXAMPLES

The following examples are provided to further illustrate the present invention. It is to be understood, however, that the examples are for purpose of illustration only and are not intended as a definition of the limits of the invention.

The following instruments were used for respective measurements.

Nuclear magnetic resonance spectrum (NMR, 270 MHz): JNM-EX 270 (manufactured by JEOL)

Internal standard $^1$H: tetramethylsilane

External standard $^{31}$P: 85% phosphoric acid

Angle of rotation: DIP-360 (manufactured by JASCO)

Gas chromatography: GC-15A gas chromatography (manufactured by Shimadzu Corp.)

Capillary column: CHROMPACK CP-Cyclodextrine-β-236M-19 (0.25 mm×25 mm)
Liquid chromatography: CO-8000 (manufactured by TOSO)
Detector: UV-8000 (manufactured by TOSO)
Column (254 nm): CHIRALCEL OD (manufactured by Daicel Chemical Industries) (25 cm×0.46 cm)
Melting point: MP-500D (manufactured by Yanako)

All experiments were carried out using Schlenk tube in an atmosphere of argon purified through a column packed with a BASF catalyst R3-11.

Oxygen-free solvents were prepared in the following manner.

Methanol: used after distillation of commercially available reagent in the presence of magnesium methoxide.

Tetrahydrofuran: used after distillation in the presence of sodium benzophenone ketyl.

SYNTHESIS EXAMPLE 1

(1) Synthesis of 2,2'-dibromo-5,5',6,6',7,7',8,8'-octahydro-1,1'-binaphthyl (compound 1)

A 500 ml capacity stainless steel autoclave was charged with 35 g (0.085 mol) of 2,2'-dibromo-1,1'-binaphthyl, 5.25 g of 5%-ruthenium-carbon (manufactured by NECHEM-CAT), 130 ml of ethyl acetate and 130 ml of 95% ethanol. After carrying out 20 hours of hydrogenation at a temperature of 100° C. under a hydrogen pressure of 50 kg/cm$^2$, absorption of 4 mols of hydrogen per mol substrate was confirmed. The reaction mixture was cooled to 30° C. to remove the catalyst by filtration, the resulting filtrate was allowed to stand overnight at room temperature and then 30.6 g of the thus precipitated crystals were collected by filtration (yield, 85.7%).

Melting point: 146°–147° C. $^1$H-NMR (CDCl$_3$) δ ppm: 1.75 (m, 8 H), 2.08 (dt, 2 H, J=17.67 Hz), 2.33 (dt, 2 H, J=17.67 Hz), 2.77 (m, 4 H), 6.98 (d, 2 H, J=8.2 Hz), 7.42 (d, 2 H, J=8.2 Hz)

(2) Synthesis of 2,2'-bis(diphenylphosphinyl)-5,5',6,6',7,7',8,8'-octahydro-1,1'-binaphthyl (compound 2)

A one liter capacity four neck flask was charged with 4.26 g (0.177 mol) of magnesium, the atmosphere in the flask was replaced with nitrogen gas and then a small amount of iodine was added thereto. To this were added 20 ml of dry tetrahydrofuran and, using an injector, 0.6 ml of 1,2-dibromoethane in that order. Through a dropping funnel and spending 7 hours, to this was added dropwise a mixture solution of 330 ml toluene and 90 ml tetrahydrofuran containing 32.5 g (0.0774 mol) of 2,2'-dibromo- 5,5',6,6',7,7',8,8'-octahydro-1,1'-binaphthalene synthesized in (1). During this step, temperature of the reaction solution was kept at 80° to 90° C. After completion of the dropwise addition, the reaction mixture was stirred at 94° C. for 19 hours. After cooling to 5° C., to the reaction mixture was added dropwise 34.27 g (0.148 mol) of diphenylphosphinic acid chloride spending 30 minutes. Next, the reaction mixture was stirred at 72° C. for 3.5 hours. The resulting reaction mixture was cooled to room temperature and mixed with 100 ml of water, heated to 80° C. and stirred for 20 minutes, and then cooled again to room temperature and allowed to stand overnight. The thus precipitated white solid was collected by filtration, washed twice with 100 ml of water, washed again with 100 ml of hexane-toluene (9:1) mixture solution and then dried at 70° C. for 7 hours under a reduced pressure (0.1 mmHg) to obtain 32.8 g of the title compound with a yield of 64.1%.

Melting point: 300° C. (decomposition) $^1$H-NMR (CDCl$_3$) δ ppm: 6.938 (d, 1 H, J=13.29 Hz), 6.958 (d, 1 H, J=13.29 Hz), 7.002 (d, 1 H, J=3.19 Hz), 7.022 (d, 1 H, J=3.19 Hz), 7.36 (m, 4 H), 7.43 (m, 4 H), 7.51 (tq, 4 H), 7.65 (dq, 4 H), 7.78 (dq, 4 H) $^-$P-NMR (CDCl$_3$) δ ppm: 28.415

(3) Optical resolution of 2,2'-bis(diphenylphosphinyl)-5,5',6,6',7,7',8,8'-octahydro-1,1'-binaphthyl (compound 2)

A 90 g (11.62 mmol) portion of the racemic compound (2) was dissolved in 2,000 ml of hot chloroform, 47.69 g (13.31 mmol) of (–)-dibenzoyltartaric acid was separately dissolved in 1,300 ml of ethyl acetate at 70° C., and both solutions thus prepared were mixed with each other with stirring. After allowing the mixture to stand overnight at room temperature, crystals thus precipitated were collected by filtration and dried at room temperature for 10 hours under a reduced pressure (0.1 mmHg) to obtain 57.94 g of the salt of interest. This was dissolved in a hot mixture solvent consisting of 700 ml of chloroform, 120 ml of ethanol and 1,400 ml of ethyl acetate, and the resulting solution was cooled to room temperature to effect precipitation of crystals which were subsequently collected by filtration and dried at room temperature under a reduced pressure (0.1 mmHg) to obtain 54.87 g of the salt of interest. This was mixed with 1,000 ml of 1.5N sodium hydroxide, extracted three times with 1,000 ml of chloroform, washed with 400 ml of 1.5N sodium hydroxide, washed three times with 1,000 ml of water, dried on anhydrous magnesium sulfate and then concentrated to obtain 32.48 g of optically active (compound 2) with a yield of 44.21%.

$[\alpha]_D^{24}$: –33.91° (C=0.5, CHCl$_3$)

Separately from this, the mother liquor formed by the resolution was mixed with 1,400 ml of 1.5N sodium hydroxide, extracted twice with 1,000 ml of chloroform and the resulting extract was dried on anhydrous magnesium sulfate. To the chloroform solution was added 28 g of (+)-dibenzoyltartaric acid which has been dissolved in 200 ml of ethyl acetate at 70° C. After overnight standing at room temperature, the crystals thus precipitated were collected by filtration and dissolved in a mixture solvent consisting of 700 ml of chloroform, 120 ml of ethanol and 1,400 ml of ethyl acetate. The resulting crystals precipitated at room temperature were collected by filtration, mixed with 1,000 ml of 1.5N sodium hydroxide, extracted three times with 1,000 ml of chloroform, washed three times with 1,000 ml of water, dried on anhydrous magnesium sulfate and then concentrated to obtain 29.8 g of optically active (compound 2) with a yield of 40.67%.

$[\alpha]_D^{24}$: +34.66° (C=0.5, CHCl$_3$)

A high performance liquid chromatography using an optically active column (CHIRALCEL OG) confirmed that the (–)-(compound 2) and (+)-(compound 2) obtained in the above manner are 98.46% ee and 100% ee, respectively.

(4) Synthesis of optically active 2,2'-bis(diphenylphosphino)-5,5',6,6',7,7',8,8'-octahydro-1,1'-binaphthyl (to be referred to as "OcH-binap" hereinafter)

A 500 ml capacity four neck flask was charged with 4.6 g (6.04 mmol) of the (–)-(compound 2). After replacing the atmosphere in the flask with nitrogen gas, to this were further added 150 ml of xylene, 3.67 g (36.24 mmol) of triethylamine and 4.91 g (36.24 mmol) of trichlorosilane. The resulting mixture was stirred at room temperature for 20 minutes, at 90° to 110° C. for 20 minutes, at 110 to 120° C. for 1 hour and then at 130° C. for 16.5 hours. To this were further added 1.88 g (13.88 mmol) of trichlorosilane and 1.38 g (13.64 mmol) of triethylamine, followed by 6 hours of stirring at 130° C. After cooling to room temperature, this was mixed with 100 ml of 3N sodium hydroxide and stirred at 60° C. for 2 hours. Thereafter, the resulting reaction solution was cooled to room temperature, its organic layer and water layer were separated from each other, and then the organic layer was dried on anhydrous magnesium sulfate and concentrated to obtain 3.49 g of (−)-(OcH-binap) with a yield of 91.7%.

$[\alpha]_D^{24}$: −72.42° (C=0.504, toluene)

Melting point: 207°–208° C. $^1$H-NMR (CDCl$_3$) δ ppm: 0.890 (m, 2 H), 1.27 (m, 2 H), 1.45 (m, 4 H), 1.54 (dt, 2 H), 1.84 (dq, 2 H), 2.64 (dt, 2 H), 2.71 (dt, 2 H), 6.88 (dt, 2 H), 7.03 (d, 2 H), 7.20 (br s, 10 H), 7.30 (m, 10 H) $^{31}$P-NMR (CDCl$_3$) δ ppm: −15.3374 Elementary analysis: (as C$_{44}$H$_{40}$P$_2$) calcd. C, 83.79%; H, 6.39% found C, 83.51%; H, 6.38%

Using (+)-(compound 2), the same procedure was repeated to obtain (+)-(OcH-binap).

$[\alpha]_D^{24}$: +72.35 (C=0.516, toluene) Melting point: 207°–208° C.

Results of $^1$H-NMR of (+)-(OcH-binap) were the same as those of (−)-(OcH-binap).

SYNTHESIS EXAMPLE 2

A 300 ml capacity side arm flask was charged with 0.236 g (0.241 mmol) of [RuI$_2$(p-cymene)]$_2$ which has been synthesized in accordance with the method of Majima et al. (*J. Chem. Soc. Commun.*, p. 1208, 1989) and 0.3035 g (0.481 mmol) of the (−)-(OcH-binap) obtained in Synthesis Example 1 (4). After replacing the atmosphere in the flask with nitrogen gas, 16 ml of methylene chloride was added and the resulting mixture was stirred at 40° C. for 2 hours. After removing methylene chloride by distillation, the resulting residue was dried at room temperature for 15 hours under a reduced pressure (0.1 mmHg) to obtain 0.58 g of ruthenium iodo-π-p-cymene-[2,2'-bis(diphenylphosphino)-5,5',6,6',7,7',8,8'-octahydro-1,1'-binaphthyl] iodide, [RuI(p-cymene)((−)-OcH-binap)]I, with a quantitative yield.

$^{31}$P-NMR (CDCl$_3$) δ ppm: 23.2418 (d), 39.7730 (d) Elementary analysis: (as C$_{54}$H$_{54}$I$_2$P$_2$Ru) calcd. C, 57.92%; H, 4.86% found C, 56.66%; H, 4.80%

SYNTHESIS EXAMPLE 3

A 200 ml capacity side arm flask was charged with 0.985 g (3.38 mmol) of [Ru(COD)Cl$_2$]$_n$ which has been synthesized in accordance with the method of Bennet et al. (*Chem. & Ind.*, p. 1516, 1959) by allowing ruthenium trichloride to react with 1,5-cyclooctadiene in ethanol, together with 2.40 g (3.81 mmol) of the (−)-OcH-binap obtained in Synthesis Example 1 (4). After replacing the atmosphere in the flask with nitrogen gas, 100 ml of toluene and 2 ml (14.35 mmol) of triethylamine were added and the resulting mixture was heated at 115° C. under reflux for 15 hours. After cooling to 30° C., toluene was distilled off under a reduced pressure (2 mmHg), and the resulting residue was dried for 10 hours in vacuo (0.1 mmHg) to obtain 3.25 g of diruthenium tetrachloro-di-[2,2'-bis(diphenylphosphino)-5,5',6,6',7,7',8,8'-octahydro-1,1'-binaphthyl] triethylamine, Ru$_2$Cl$_4$((−)-OcH-binap)$_2$(NEt$_3$), with a quantitative yield of 100%.

$^{31}$P-NMR (CDCl$_3$) δ ppm: 44.78 (d), 51.34 (d) Elementary analysis: (as C$_{94}$H$_{95}$Cl$_4$NP$_4$Ru$_2$) calcd. C, 66.16%; H, 5.61% found C, 67.03%; H, 5.78%

SYNTHESIS EXAMPLE 4

A 200 ml capacity side arm flask was charged with 1.94 g (1.14 mmol) of Ru$_2$Cl$_4$((−)-OcH-binap)$_2$(NEt$_3$) obtained in Synthesis Example 3 and 0.984 g (12 mmol) of sodium acetate. After replacing the atmosphere in the flask with nitrogen gas, 50 ml of tert-butanol was added and the resulting mixture was heated at 85° C. under reflux for 10 hours. After cooling to 50° C., tert-butanol was removed by distillation under a reduced pressure of 20 mmHg to obtain a dark green solid. The solid was mixed with 30 ml of ethanol to collect the resulting soluble fraction, the residue was again mixed with 30 ml of ethanol to collect the resulting soluble fraction, and then the soluble fractions were combined and concentrated to dryness. This was mixed with 8 ml of toluene and heated under reflux, and the resulting soluble fraction was collected, mixed with 16 ml of n-hexane and then allowed to stand overnight in a refrigerator. Thereafter, the thus precipitated solid was collected by filtration and dried at room temperature under a reduced pressure (0.1 mmHg) to obtain 1.48 g of ruthenium [2,2'-bis(diphenylphosphino)-5,5',6,6',7,7',8,8'-octahydro-1,1'-binaphthyl] diacetate, Ru(OAc)$_2$((−)-OcH-binap), with a yield of 76.4%.

$^{31}$P-NMR (CDCl$_3$) δ ppm: 64.18 Elementary analysis: (as C$_{48}$H$_{46}$O$_4$O$_2$Ru) calcd. C, 67.83%; H, 5.46% found C, 67.98%; H, 5.65%

SYNTHESIS EXAMPLE 5

A 100 ml capacity side arm flask was charged with 0.2 g (0.4 mmol) of [Ru(C$_6$H$_6$)Cl$_2$]$_2$ which has been synthesized in accordance with the method of Majima et al. (*J. Chem. Soc. Chem. Commun.*, p. 1208, 1989) and 0.505 g (0.8 mmol) of the (−)-OcH-binap obtained in Synthesis Example 1 (4). After replacing the atmosphere in the flask with nitrogen gas, 90 ml of ethanol and 12 ml of benzene were added and the resulting mixture was stirred at 50° C. for 45 minutes. After removing insoluble materials by filtration, the resulting filtrate was concentrated to obtain 0.62 g of ruthenium dichloro-p-benzene-[2,2'-bis(diphenylphosphino)-5,5',6,6',7,7',8,8'-octahydro-1,1'-binaphthyl], [Ru(C$_6$H$_6$)((−)-OcH-binap)]Cl, with a yield of 87.9%.

$^1$H-NMR (CDCl$_3$) δ ppm: 0.95–2.60 (m, 16 H), 5.59 (s, 6 H), 6.06 (d, 1 H), 6.89 (d, 1 H), 7.15–7.43 (m, 6 H), 7.48 (m, 8 H), 7.72 (d, 1 H) $^{31}$P-NMR (CDCl$_3$) δ ppm: 28.14 (d), 37.19 (d)

EXAMPLE 1

Asymmetric Hydrogenation of Tiglic Acid

In an atmosphere of argon, 8.2 mg (9.6×10$^{-3}$ mmol) of Ru(OAc)$_2$[(S)-(−)-OcH-binap] complex and 192.5 mg (1.92 mmol) of tiglic acid were dissolved in 9.6 ml of methanol, and the resulting solution was put into a 100 ml capacity autoclave and stirred at 25° C. for 37 hours under a hydrogen pressure of 1.5 atm. The reaction solution was concentrated under a reduced pressure of 20 mmHg, the resulting residue was subjected to distillation using Kugelrohr, and the thus obtained compound was checked for its proton NMR to find that it was pure (S)-2-methylbutanoic acid. A total of 142.8 mg (0.37 mmol) of the compound was obtained with a yield of 73%.

A 37.7 mg (0.37 mmol) portion of the thus obtained compound was allowed to react with 51.1 mg of aniline in the coexistence of 8 mg of 4-dimethylaminopyridine, 91.4 mg of N,N'-dicyclohexylamide and 5 ml of tetrahydrofuran, the precipitate formed by the reaction was separated by filtration and then the thus obtained filtrate was concentrated. The resulting residue was purified by a silica gel column chromatography to obtain quantitative amount of 2-methylbutanoic acid anilide. When optical purity of the thus obtained anilide was determined using CHIRAL COLUMN:CHIRALCEL OD, its asymmetric yield was found to be 97% ee.

Analytical conditions: eluting solution, hexane/2-propanol=97/3; flow rate, 0.5 ml/min; tR (retention time)=64.37 (S), tR=68.92 (R); and detector, UV 254 nm.

EXAMPLE 2

Asymmetric hydrogenation of trans-2-methyl-2-pentenoic acid

In an atmosphere of argon, 14.3 mg ($16.8 \times 10^{-3}$ mmol) of Ru(OAc)$_2$[(S)-(–)-OcH-binap] complex and 409 mg (3.58 mmol) of trans-2-methyl-2-pentenoic acid were dissolved in 18 ml of methanol, and the resulting solution was put into a 100 ml capacity autoclave and stirred at 25° C. for 24 hours under a hydrogen pressure of 1.5 atm. The reaction solution was concentrated under a reduced pressure and then subjected to distillation under a reduced pressure to obtain 370 mg of (S)-2-methylpentanoic acid with a yield of 89%.

$[\alpha]_D^{24}$: +17.56° (neat)

Reported $[\alpha]_D^{16}$: +18.4° (neat) ((S)-2-methylpentanoic acid)

When measured by a gas chromatography using CHROMPACK CP-Cyclodextrine-β-236M-19, its optical purity was found to be 96% ee. Measuring conditions: 100° C., carrier gas (He) 1.0 kg/cm$^2$, tR=16.8 (S) and tR=19.59 (R)

EXAMPLE 3

Asymmetric hydrogenation of trans-2-ethyl-2-hexenoic acid

In an atmosphere of argon, 7.2 mg ($8.5 \times 10^{-3}$ mmol) of Ru(OAc)$_2$[(S)-(–)-OcH-binap] complex and 233.5 mg (1.64 mmol) of trans-2-ethyl-2-hexenoic acid were dissolved in 8.2 ml of methanol, and the resulting solution was put into a 100 ml capacity autoclave and stirred at 25° C. for 37 hours under a hydrogen pressure of 1.5 atm. The reaction solution was concentrated and subjected to distillation to obtain 186.1 mg of (R)-2-ethylhexanoic acid with a yield of 79%.

$[\alpha]_D^{24}$: +8.52° (neat)

Reported $[\alpha]_D^{25}$: –4.2° (neat) ((R)-2-ethylhexanoic acid)

When measured by a gas chromatography using a capillary column packed with CHROMPACK CP-Cyclodextrine-β-236M-19, its optical purity was found to be 95% ee.

EXAMPLE 4

Asymmetric hydrogenation of 3-trifluoromethylcrotonic acid

In an atmosphere of argon, 12 mg ($14.1 \times 10^{-3}$ mmol) of Ru(OAc)$_2$[(S)-(–)-OcH-binap] complex and 434.7 mg (2.82 mmol) of 3-trifluoromethylcrotonic acid were dissolved in 14 ml of methanol, and the resulting solution was put into a 100 ml capacity autoclave and stirred at 25° C. for 63 hours under a hydrogen pressure of 100 atm. The reaction solution was concentrated and then subjected to distillation to obtain 376 mg of (–)-3-trifluoromethylbutanoic acid with a yield of 85%.

$[\alpha]_D^{22}$: –19.88° (c 1.02, CHCl$_3$)

Its optical purity was found to be 87% ee when it was condensed with aniline and the resulting amide compound was checked by HPLC using CHIRALCEL OD.

EXAMPLE 5

Asymmetric hydrogenation of 2-(4-isobutylphenyl)propenoic acid

In an atmosphere of argon, 4.6 mg ($5.4 \times 10^{-3}$ mmol) of Ru(OAc)$_2$[(S)-(–)-OcH-binap] complex and 220.4 mg (1.08 mmol) of 2-(4-isobutylphenyl)-propenoic acid were dissolved in 5.4 ml of methanol, and the resulting solution was put into a 100 ml capacity autoclave and stirred at 25° C. for 24 hours under a hydrogen pressure of 100 atm. The reaction solution was concentrated and then subjected to a silica gel column chromatography (eluting solution, ether) to obtain 211 mg of (S)-2-(4-isobutylphenyl)propionic acid with a yield of 94%.

$[\alpha]_D^{22}$: +47.8° (c 1.98, ethanol)

Reported $[\alpha]_D^{20}$: +59° (c 2, ethanol)

When measured using an optically active chiral column (CHROMPACK CP-Cyclodextrine-β-236M-19), its optical purity was found to be 99% ee.

EXAMPLE 6

Asymmetric hydrogenation of 2-phenylcinnamic acid

In an atmosphere of argon, 7.2 mg ($8.5 \times 10^{-3}$ mmol) of Ru(OAc)$_2$[(S)-(–)-OcH-binap] complex and 382.3 mg (1.7 mmol) of 2-phenylcinnamic acid were dissolved in 8.5 ml of methanol, and the resulting solution was put into a 100 ml capacity autoclave and stirred at 60° C. for 15 hours under a hydrogen pressure of 25 atm. The reaction solution was concentrated and then purified by a silica gel column chromatography to obtain 375.2 mg of (R)-2,3-diphenylpropanoic acid with a yield of 98%.

$[\alpha]_D^{24}$: –87.35° (C 0.525, acetone)

Its optical purity was found to be 63% ee when it was condensed with aniline and the resulting amide compound was checked by HPLC using CHIRALCEL OD.

EXAMPLE 7

Asymmetric hydrogenation of trans-2-methyl-2-hexenoic acid

In an atmosphere of nitrogen, 3.5 mg ($3.1 \times 10^{-3}$ mmol) of [RuI(p-cymene)((S)-(–)-OcH-binap]I complex and 2 g (15.6 mmol) of trans-2-methyl-2-hexane were dissolved in 10 ml of methanol to which was subsequently added 1 ml of water. The resulting homogeneous solution was put into a 100 ml capacity autoclave and stirred at 50° C. for 6 hours under a hydrogen pressure of 4 atm. The reaction solution was concentrated and then subjected to distillation to obtain 1.77 g of (S)-2-methylhexanoic acid with a yield of 87%.

When the thus obtained compound was converted into amide of (R)-(+)-α-phenylethylamine and then measured by a capillary gas chromatography (column: NUTRABOND-1 manufactured by GL SCIENCE INC., 30 m×0.25 mm), its optical purity was found to be 94% ee.

EXAMPLE 8

Asymmetric hydrogenation of tiglic acid

In an atmosphere of nitrogen, 33.8 mg ($3\times10^{-2}$ mmol) of [RuI(p-cymene)((S)-(−)-OcH-binap]I complex and 3 g (30 mmol) of tiglic acid were dissolved in 1.5 ml of water and 15 ml of methanol, and the resulting solution was put into a 100 ml capacity autoclave and stirred at 50° C. for 6 hours under a hydrogen pressure of 4 atm. The reaction solution was concentrated and then subjected to distillation to obtain 2.6 g of (S)-2-methylbutanoic acid with a yield of 85%. When measured in the same manner as described in Example 1, its optical purity was found to be 96% ee.

EXAMPLES 9 TO 21

Optically active carboxylic acids shown in Table 1 were produced in the same manner as described in Examples 1 to 8, with the results also shown in Table 1. In the table, $R^1$ to $R^3$ are the groups of formula (I).

TABLE 1

| | Formula (I) | | | | temp. |
|---|---|---|---|---|---|
| Example | $R^1$ | $R^2$ | $R^3$ | Catalyst | S/C | (°C.) |
| 9 | Me | Me | H | (R)-3 | 200 | 25 |
| 10 | Me | Me | H | (S)-2 | 200 | 25 |
| 11 | Me | Me | H | (S)-2 | 200 | 25 |
| 12 | Me | Me | H | (S)-2 | 200 | 25 |
| 13 | Me | Et | H | (S)-2 | 213 | 25 |
| 14 | Et | Pr | H | (S)-2 | 192 | 25 |
| 15 | Et | Pr | H | (S)-2 | 193 | 25 |
| 16 | Et | Pr | H | (R)-4 | 98 | 25 |
| 17 | H | $CF_3$ | Me | (S)-2 | 200 | 25 |
| 18 | 4-i-Bu-$C_6H_4$ | H | H | (S)-2 | 200 | 60 |
| 19 | 4-i-Bu-$C_6H_4$ | H | H | (S)-2 | 200 | 25 |
| 20 | 4-i-Bu-$C_6H_4$ | H | H | (S)-2 | 200 | 25 |
| 21 | 4-i-Bu-$C_6H_4$ | H | H | (S)-2 | 200 | 25 |

| Example | $PH_2$ (atm) | Time (h) | Conversion (%) | Isolated Yield (%) | e.e. (%) | Config. |
|---|---|---|---|---|---|---|
| 9 | 4 | 15 | 94 | 73 | 94(99) | R |
| 10 | 4 | 14 | 100 | 91 | 94 | S |
| 11 | 4 | 15 | 100 | 83 | 96 | S |
| 12 | 1.5 | 37 | 100 | 73 | 97 | S |
| 13 | 1.5 | 24 | 100 | 89 | 96 | S |
| 14 | 4 | 15 | 100 | 91 | 94 | S |
| 15 | 1.5 | 37 | 100 | 79 | 95 | S |
| 16 | 1.5 | 37 | 100 | 100 | 90 | R |
| 17 | 100 | 63 | 100 | 85 | 87 | (−) |
| 18 | 106 | 6 | 100 | 99 | 87 | S |
| 19 | 100 | 24 | 100 | 94 | 97 | S |
| 20 | 25 | 24 | 100 | 99 | 94 | S |
| 21 | 100 | 8 | 100 | 97 | 97 | S |

S/C, substrate/catalyst molar ratio; $PH_2$, hydrogen pressure; conversion ratio, measured by $^1$H-NMR; config, absolute configuration; Me, methyl; Et, ethyl; Pr, propyl; Bu, butyl; (S)-2, Ru(OAc)$_2$[(S)-OcH-binap]; (R)-3, [RuI((R)-OcH-binap)(p-cymene)]I; (R)-4, Ru(OAc)$_2$[(R)-Cy-binap]

COMPARATIVE EXAMPLE 1

Asymmetric hydrogenation of trans-2-methyl-2-hexenoic acid

In an atmosphere of argon, 9.94 mg ($16.3\times10^{-3}$ mmol) of Ru(OAc)$_2$[(R)-binap] complex [wherein "(R)-binap" represents "(R)-2,2'-diphenylphosphino-1,1'-binaphthyl"] and 409 mg (3.58 mmol) of trans-2-methyl-2-hexenoic acid were dissolved in methanol, and the resulting solution was put into a 100 ml capacity autoclave and stirred at 25° C. for 24 hours under a hydrogen pressure of 1.5 atm. The reaction solution was concentrated and then subjected to distillation to obtain 286.9 mg of (R)-2-methylhexanoic acid with a yield of 69%. Its optical purity was found to be 84% ee.

COMPARATIVE EXAMPLES 2 AND 3

Using substrates shown in Table 2, the procedure of Comparative Example 1 was repeated, with the results also shown in Table 2.

TABLE 2

| Comp. Ex. | Substrate | Temp. (°C.) | $PH_2$ (atm) | Time | Yield | e.e. (%) | Config. |
|---|---|---|---|---|---|---|---|
| 2 | 2-methyl-2-hexenoic acid | 25 | 1.5 | 37 | 95 | 88 | R |
| 3 | 2-(4-isobutyl-phenyl) propenoic acid | 60 | 27 | 15 | 99 | 75 | S |

$PH_2$, hydrogen pressure; Config., absolute configuration

EXAMPLES 22 TO 35 AND COMPARATIVE EXAMPLES 4 TO 7

Reaction was carried out in the same manner as in Example 1, except that the substrate, catalyst, hydrogen pressure, and other conditions were changed as shown in Table 3 and except the other changes stated below.

TABLE 3

| | Formula (I) | | | | | $PH_2$ | Time |
|---|---|---|---|---|---|---|---|
| Example | $R^1$ | $R^2$ | $R^3$ | Catalyst | S/C | (atm) | (h) |
| 22 | Me | H | Me | (S)-2 | 200 | 4.0 | 15 |
| 23 | Me | H | Me | (S)-2 | 200 | 1.5 | 20 |
| 24 | Me | H | Me | (R)-3 | 200 | 4.0 | 15 |
| 25 | Pr | H | Me | (S)-2 | 213 | 1.5 | 24 |
| 26 | Pr | H | Me | (S)-2 | 201 | 1.5 | 20 |
| 27[f] | Pr | H | Me | (S)-2 | 204 | 1.5 | 22 |
| 28[f,g] | Pr | H | Me | (S)-2 | 205 | 1.5 | 6 |
| 29[f,g] | Pr | H | Me | (S)-2 | 209 | 4.0 | 3 |
| 30 | Pr | H | Et | (S)-2 | 197 | 1.5 | 20 |
| 31 | Pr | H | Et | (S)-2 | 192 | 4.0 | 15 |
| 32 | Ph | H | Me | (S)-2 | 200 | 1.5 | 48 |
| 33[h] | Ph | H | Me | (S)-2 | 200 | 1.8 | 26 |
| 34[h] | Ph | H | Me | (S)-2 | 200 | 25 | 15 |
| 35h | Ph | H | Me | (S)-2 | 200 | 97 | 8 |
| Comp. Ex. 4 | Et | H | Me | (R)-1a[i] | 220 | 1.5 | 24 |
| Comp. Ex. 5[f,g] | Pr | H | Me | (R)-1a | 1000 | 4.0 | 4 |
| Comp. Ex. 6 | Pr | H | Et | (R)-1a | 203 | 1.5 | 37 |
| Comp. Ex. 7[h] | Ph | H | Me | (R)-1a | 200 | 25 | 15 |

| Example | Conversion[a] (%) | Isolated Yield[b] (%) | e.e.[c] (%) | Config.[d] |
|---|---|---|---|---|
| 22 | 100 | 83 | 96 | S |
| 23 | 100 | 85 | 97 | S |
| 24 | 94 | 73 | 96 | R |
| 25 | 100 | 89 | 96[e] | S |
| 26 | 100(99.5) | 98 | 94 | S |
| 27[f] | 100(100) | 90 | 96 | S |

TABLE 3-continued

| | | | | |
|---|---|---|---|---|
| 28[f,g] | 100(100) | 88 | 94 | S |
| 29[f,g] | 100(100) | 83 | 94 | S |
| 30 | 100 | 80 | 95[e] | S |
| 31 | 100 | 91 | 94[e] | S |
| 32 | 95 | 87 | 89 | S |
| 33[h] | 100 | 93 | 86 | S |
| 34[h] | 100 | 82 | 82 | S |
| 35[h] | 100 | 91 | 75 | S |
| Comp. Ex. 4 | 75 | 69 | 84[e] | R |
| Comp. Ex. 5[f,g] | 100(100) | 86 | 82 | R |
| Comp. Ex. 6 | 100 | 95 | 88[e] | R |
| Comp. Ex. 7[h] | 100 | 89 | 35 | R |

Hydrogenation was carried out in an autoclave at 10°–25° C. in methanol unless otherwise stated.
a: As given by 1H-NMR analysis. Values in parentheses were obtained on GLC analysis with a NEUTRA BOND-1 capillary column.
b: Isolation yield obtained on kugelrohr distillation.
c: Enantiomeric excesses determined by HPLC analysis of the anilides of the saturated carboxylic acids with a DAICEL CHIRALCEL OB or OD column unless otherwise indicated.
d: Absolute configurations were determined by the signs of optical rotation.
e: Measured by GLC analysis of the saturated carboxylic acids with a CHROMPACK CP-cyclodextrine-β-236M-19 capillary column.
f: Solvent system was MeOH-H$_2$O (10:1)
g: Reaction temperature was 50° C.
h: Reaction temperature was 60° C.
i: (R)-1a indicates the ruthenium-optically active phosphine complex represented by formula (XIII):

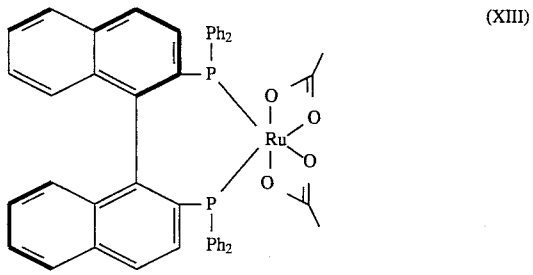

wherein Ph represents a phenyl group.

While the invention has been described in detail and with reference to specific embodiments thereof, it will be apparent to one skilled in the art that various changes and modifications can be made therein without departing from the spirit and scope thereof.

What is claimed is:

1. A process for producing an optically active carboxylic acid represented by formula (I)

wherein R$^1$, R$^2$ and R$^3$ each represents a hydrogen atom, an alkyl group which may have a substituent group or an aromatic hydrocarbon group which may have a substituent group, with the proviso that R$^1$, R$^2$ and R$^3$ are not hydrogen atoms at the same time, that R$^3$ is a group other than methyl when R$^1$ and R$^2$ are hydrogen atoms at the same time, and that R$^1$ and R$^2$ are different groups other than a hydrogen atom when R$^3$ is a hydrogen atom, said process comprising subjecting an olefinic carboxylic acid represented by formula (II)

wherein R$^1$, R$^2$ and R$^3$ are the same as defined above to asymmetric hydrogenation using a complex as a catalyst which consists of a ruthenium compound and an optically active phosphine represented by formula (III)

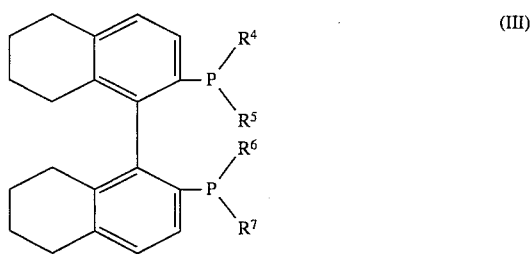

wherein R$^4$, R$^5$, R$^6$ and R$^7$ may be the same or different from one another and each represents a phenyl group which may be substituted with an alkyl group having 1 to 4 carbon atoms, an alkoxy group having 1 to 4 carbon atoms or a halogen atom, a cyclopentyl group or a cyclohexyl group.

2. A process for producing an optically active carboxylic acid represented by formula (I)

wherein R$^1$, R$^2$ and R$^3$ each represents a hydrogen atom, an alkyl group which may have a substituent group or an aromatic hydrocarbon group which may have a substituent group, with the proviso that R$^1$, R$^2$ and R$^3$ are not hydrogen atoms at the same time, that R$^3$ is a group other than methyl when R$^1$ and R$^2$ are hydrogen atoms at the same time, and that R$^1$ and R$^2$ are different groups other than a hydrogen atom when R$^3$ is a hydrogen atom, said process comprising subjecting an olefinic carboxylic acid represented by formula (II)

wherein R$^1$, R$^2$ and R$^3$ are the same as defined above to asymmetric hydrogenation in the presence of both a ruthenium compound and an optically active phosphine represented by formula (III)

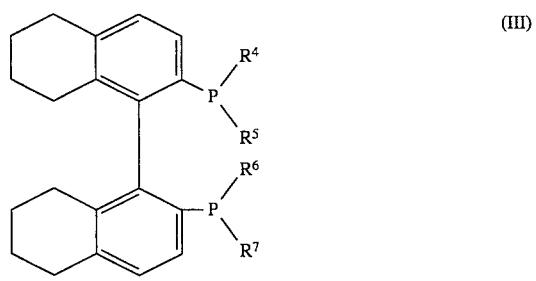

wherein R$^4$, R$^5$, R$^6$ and R$^7$ may be the same or different from one another and each represents a phenyl group which may be substituted with an alkyl group having 1 to 4 carbon atoms, an alkoxy group having 1 to 4 carbon atoms or a halogen atom, a cyclopentyl group or a cyclohexyl group.

3. The process as claimed in claim 1, wherein the ruthenium compound is one selected from the group consisting of a compound represented by formula (VIII):

$[RuX_2 2Q^1]_n$     (VIII)

wherein X represents a halogen atom, an allyl group, or a methallyl group, $Q^1$ represents 1,5-cyclooctadiene, norbornadiene, benzene, or p-cymene, and n represents a natural number;

and a compound represented by formula (IX):

$RuA_3$     (IX)

wherein A represents acetylacetonato or an acetoxy group.

4. The process as claimed in claim 2, wherein the ruthenium compound is one selected from the group consisting of a compound represented by formula (VIII):

$[RuX_2Q^1]_n$     (VIII)

wherein X represents a halogen atom, an allyl group, or a methallyl group, $Q^1$ represents 1,5-cyclooctadiene, norbornadiene, benzene, or p-cymene, and n represents a natural number;

and a compound represented by formula (IX):

$RuA_3$     (IX)

wherein A represents acetylacetonato or an acetoxy group.

5. The process as claimed in claim 1, wherein the complex is one selected from the group consisting of a compound represented by formula (X):

$Ru_2Y_4LA$     (X)

wherein Y represents a halogen atom, L represents an optically active phosphine represented by formula (III):

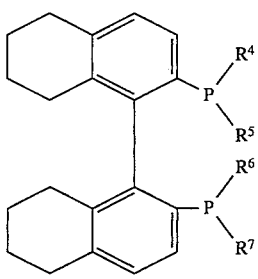
(III)

wherein $R^4$, $R^5$, $R^6$, and $R^7$ may be the same or different and each represents a phenyl group which may be substituted with an alkyl group having 1 to 4 carbon atoms, an alkoxy group having 1 to 4 carbon atoms, or a halogen atom, a cyclopentyl group, or a cyclohexyl group, and A represents a tertiary amine;

a compound represented by formula (XI):

$RuZ_2L$     (XI)

wherein Z represents an acetoxy group, an acetylacetonato group, an allyl group, or a methallyl group and L is the same as defined above; and a compound represented by formula (XII):

$[RuYQ^2L]Y$     (XII)

wherein Y and L are the same as defined above and $Q^2$ represents p-cymene or benzene.

* * * * *